(12) United States Patent
Zimmer et al.

(10) Patent No.: US 10,610,841 B1
(45) Date of Patent: Apr. 7, 2020

(54) MARKER HAVING ENHANCED ULTRASOUND VISIBILITY AND METHOD OF MANUFACTURING THE SAME

(71) Applicant: Devicor Medical Products, Inc., Cincinnati, OH (US)

(72) Inventors: Timothy Zimmer, Centerville, OH (US); Michelle Louise Johnson, Moscow, OH (US); Stephen D. Stallard, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 220 days.

(21) Appl. No.: 15/636,126

(22) Filed: Jun. 28, 2017

Related U.S. Application Data

(60) Provisional application No. 62/357,186, filed on Jun. 30, 2016.

(51) Int. Cl.
*B01F 11/00* (2006.01)
*B01F 3/04* (2006.01)
(Continued)

(52) U.S. Cl.
CPC .......... *B01F 11/0071* (2013.01); *A61B 90/39* (2016.02); *A61K 49/226* (2013.01); *B01F 3/04439* (2013.01); *B01F 15/00311* (2013.01); *A61B 8/481* (2013.01); *A61B 2090/3908* (2016.02); *A61B 2090/3925* (2016.02);
(Continued)

(58) Field of Classification Search
CPC ............ B01F 11/0071; B01F 15/00311; B01F 3/04439; B01F 2215/0034; A61B 90/39;
A61B 2090/3987; A61B 2090/3925; A61B 2090/3933; A61B 2090/3908; A61B 8/481; A61K 49/226; A61K 49/04; A61K 49/1803; C08J 9/30; C08J 2300/16; C08J 2207/10; C08J 2205/022; A61L 31/18; A61L 31/145; A61L 31/148; A61L 31/146
See application file for complete search history.

(56) References Cited

U.S. PATENT DOCUMENTS 6,083,524 A 7/2000 Sawhney et al.
6,162,241 A 12/2000 Coury et al.
(Continued)

OTHER PUBLICATIONS

Ahmed, E.M., "Hydrogel: Preparation, characterization, and applications: A review," Journal of Advanced Research, 2015, 6:105-121, 17 pgs.

(Continued)

*Primary Examiner* — Stephen Hobson
(74) *Attorney, Agent, or Firm* — Frost Brown Todd LLC

(57) ABSTRACT

A method and system are used to enhance a marker material to include a plurality of air bubbles. The method of manufacturing a marker includes enhancing a marker material to include a plurality of air bubbles using at least a first EFD and a second EFD. The method may include cycling repeatedly through a transfer process between a first container and a second container. A system for enhancing a marker material includes a transfer apparatus configured to receive a marker material and a selected amount of air. The system comprises a first EFD coupled to a first end of the transfer apparatus and a second EFD coupled to a second end of the transfer apparatus.

8 Claims, 9 Drawing Sheets

(51) Int. Cl.
*B01F 15/00* (2006.01)
*A61K 49/22* (2006.01)
*A61B 90/00* (2016.01)
*A61B 8/08* (2006.01)
*A61L 31/18* (2006.01)
*A61L 31/14* (2006.01)
*A61K 49/18* (2006.01)
*A61K 49/04* (2006.01)
*C08J 9/30* (2006.01)

(52) U.S. Cl.
CPC .............. *A61B 2090/3933* (2016.02); *A61B 2090/3987* (2016.02); *A61K 49/04* (2013.01); *A61K 49/1803* (2013.01); *A61L 31/145* (2013.01); *A61L 31/146* (2013.01); *A61L 31/148* (2013.01); *A61L 31/18* (2013.01); *B01F 2215/0034* (2013.01); *C08J 9/30* (2013.01); *C08J 2205/022* (2013.01); *C08J 2207/10* (2013.01); *C08J 2300/16* (2013.01)

(56) References Cited

U.S. PATENT DOCUMENTS

| | | |
|---|---|---|
| 6,270,464 B1 | 8/2001 | Fulton, III et al. |
| 6,356,782 B1 | 3/2002 | Sirimanne et al. |
| 6,605,294 B2 | 8/2003 | Sawhney |
| 6,790,185 B1 | 9/2004 | Fisher et al. |
| RE39,713 E | 7/2007 | Sawhney et al. |
| 7,565,191 B2* | 7/2009 | Burbank ............. A61K 49/006 600/414 |
| 7,651,505 B2* | 1/2010 | Lubock ............. A61M 37/0069 600/431 |
| 7,877,133 B2* | 1/2011 | Burbank ............. A61K 49/226 600/431 |
| 8,320,993 B2 | 11/2012 | Sirimanne et al. |
| 8,600,481 B2 | 12/2013 | Sirimanne et al. |
| 8,639,315 B2* | 1/2014 | Burbank ............. A61K 49/226 600/432 |
| 8,939,910 B2 | 1/2015 | Fisher |
| 8,965,486 B2* | 2/2015 | Burbank ............. A61K 49/006 600/431 |
| 9,339,248 B2* | 5/2016 | Tout ................. A61K 49/0409 |
| 10,045,832 B2* | 8/2018 | Burbank ............. A61B 90/39 |
| 2006/0122503 A1* | 6/2006 | Burbank ............. A61K 49/006 600/431 |
| 2015/0133779 A1* | 5/2015 | Yurek ............. A61M 11/008 600/435 |
| 2019/0008606 A1* | 1/2019 | Ahn ................. A61B 90/39 |
| 2019/0090978 A1* | 3/2019 | Nock ................. A61B 90/39 |

OTHER PUBLICATIONS

Hahn, M., et al., "Vacuum-Assisted Breast Biopsy with Mammotome®," Devicor Medical Germany GmbH, published in Germany by Springer Medizin Verlag, 2013, 130 pgs.

Klein, R.L. et al., "Evaluation of a Hydrogel Based Breast Biopsy Marker (HydroMARK®) as an Alternative to Wire and Radioactive Seed Localization for Non-Palpable Breast Lesions," Journal of Surgical Oncology, 2012, 105(6):591-594, 4 pgs.

U.S. Appl. No. 62/357,186, filed Jun. 30, 2016.

* cited by examiner

MARKER HAVING ENHANCED ULTRASOUND VISIBILITY AND METHOD OF MANUFACTURING THE SAME

PRIORITY

The present application claims priority to U.S. Provisional Patent Application No. 62/357,186, entitled "Method for Enhancing Ultrasound Visibility of a Marker," filed on Jun. 30, 2016, the disclosure of which is hereby incorporated by reference in its entirety.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (typically a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The state of the art technology for conducting a breast biopsy is to use a vacuum-assisted breast biopsy device. A current textbook in this area is "Vacuum-Assisted Breast Biopsy with Mammotome®", available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

A biopsy marker may comprise hydrogel, such as described in "Evaluation of a Hydrogel Based Breast Biopsy Marker HydroMARK® as an Alternative to Wire and Radioactive Seed Localization for Non-Palpable Breast Lesions" by Rebecca L. Klein et al.; Journal of Surgical Oncology 2012; 105: 591-594, the contents of which are incorporated herein by reference.

Additional details regarding hydrogel are described in "Hydrogel: Preparation, characterization, and applications: A review" by Enas M. Ahmed; Journal of Advanced Research (2015) 6; 105-121, the contents of which are incorporated herein by reference.

The use of hydrogel materials for markers used after breast biopsies to mark the location where the biopsied tissue was removed is described and claimed in the following US Patents: U.S. Pat. No. 6,083,524, "Polymerizable biodegradable polymers including carbonate or dioxanone linkages" issued Jul. 4, 2000; U.S. Pat. No. 6,162,241, "Hemostatic tissue sealants", issued Dec. 4, 2000; U.S. RE39713, "Polymerizable biodegradable polymers including carbonate or dioxanone linkages issued Jul. 3, 2007; U.S. Pat. No. 6,270,464, "Biopsy localization method and device", issued Aug. 7, 2001; U.S. Pat. No. 6,356,782, "Subcutaneous cavity marking device and method", issued Mar. 12, 2002; U.S. Pat. No. 6,605,294, "Methods of using in situ hydration of hydrogel articles for sealing or augmentation of tissue or vessels", issued Aug. 12, 2003; U.S. Pat. No. 6,790,185, "Sealant plug delivery methods", issued Sep. 14, 2004; U.S. Pat. No. 8,320,993 "Subcutaneous cavity marking device", issued Nov. 27, 2012; U.S. Pat. No. 8,600,481, "Subcutaneous cavity marking device", issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

U.S. Pat. No. 8,939,910, "Method of Enhancing Ultrasound Visibility of Hyperechoic Materials", issued on 27 Jan. 2015 and assigned to Devicor Medical Products, Inc., the contents of which having previously been incorporated herein by reference, describes a hydrogel marker that is enhanced by air cavities within the hydrogel that reflect under ultrasound imaging in different way than the reflection of the hydrogel, thereby making it easier to detect the hydrogel marker. Such air cavities in the enhanced hydrogel are hypoechoic and thus serve to further indicate the location of the marker. U.S. Pat. No. 8,939,910 gives an example of creating air cavities using inserts of differing sizes and shapes. The inserts are placed in the hydrogel during the manufacturing process and removed from the hydrogel after it is cured, leaving air-filled cavities in the hydrogel marker. The cavities are air-filled and reflecting differently under ultrasound imaging from the reflection of the hydrogel and making the hydrogel easier to detect under ultrasound.

In some contexts, a marker element is disposed within a bioabsorbable carrier. In these contexts, it may be desirable to enhance the visibility of the carrier under ultrasonic visualization. One method of enhancing visualization of the carrier is impregnating the carrier with a plurality of microbubbles. However, some difficulties have been encountered with uniformly distributing microbubbles of a sufficient size throughout the carrier. Accordingly, in some contexts, it may be desirable to enhance a biopsy site marker by uniformly distributing microbubbles of a sufficient size throughout a carrier. While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1A:
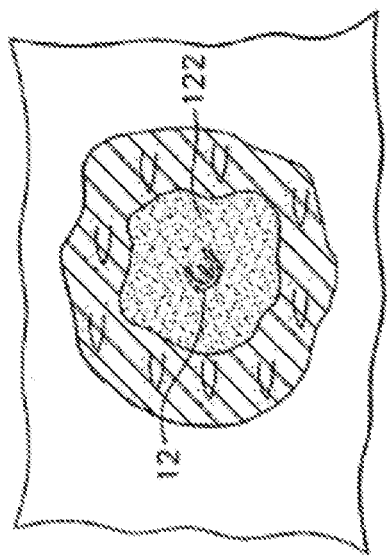
FIGS. 1A, 1B, and 1C illustrate example aspects of placement of a marker device, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

Figure 1B:
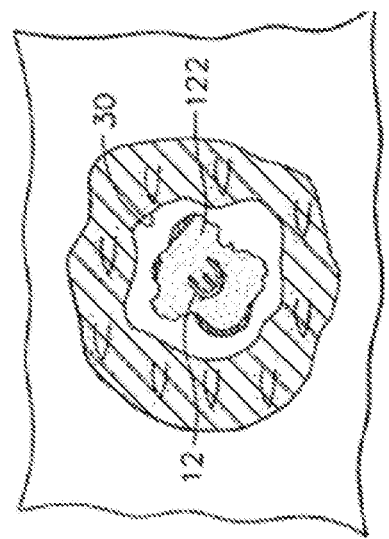
Figure 1C:
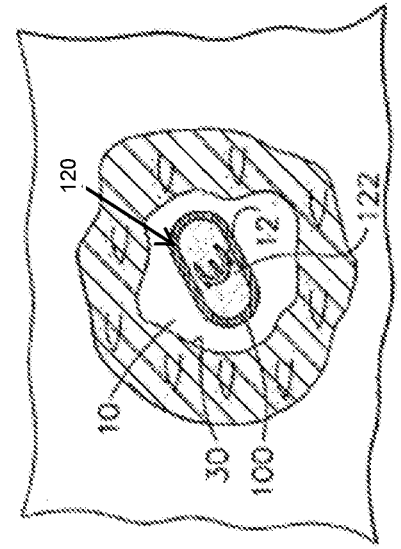

Aspects presented herein relate to devices and procedures for manufacturing a marker for percutaneously marking a biopsy cavity (10) having surrounding tissue (30), as illustrated in FIGS. 1A-C. For instance, as seen in FIG. 1A, a marker (100) may be initially placed in the biopsy cavity (10) to facilitate relocation of the biopsy site. Marker (100) may comprise a carrier (120), which includes a marker material (122) that has been enhanced to comprise a plurality of bubbles or microbubbles. As will be described in greater detail below, such bubbles may be generally desirable to provide enhanced reflection of ultrasonic radiation from the interior and exterior of marker (100). As will be described in greater detail below, marker material (122) is generally bioabsorbable such that marker material (122) may be generally absorbed into the patient's tissue over time.

In the present example, marker (100) further includes a marker element (12) that is not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12).

As described above, carrier (120) of marker (100) may comprise a bioabsorbable marker material (122). In the present example, marker material (122) comprises a hydrogel that is initially in a dehydrated state. Although a hydrogel is used in the present example, it should be understood that in other examples marker material (122) may comprise other known bioabsorbable materials.

In the present example, marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition. Marker (100) may be inserted into the body either surgically via an opening in the body cavity (30), or through a minimally invasive procedure using such devices as a catheter, introducer or similar type insertion device. Marker (100) is typically delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) is preferably large enough to be readily visible to the physician under x-ray or ultrasonic viewing, for example, yet be small enough to be able to be percutaneously deployed into the biopsy cavity and to not cause any difficulties with the patient.

Although examples are described in connection with treatment and diagnosis of breast tissue, aspects presented herein may be used for markers in any internal, preferably soft, tissue, e.g., in breast tissue, lung tissue, prostate tissue, lymph gland tissue, etc.

Many properties of a marker material affect the intensity of its ultrasound reflection, including density, physical structure, molecular material, and shape. For example, sharp edges, or multiple reflecting surfaces on or within an object differing in density from its surroundings enhances a marker's ability to be detected by ultrasound. Interfaces separating materials of different densities, such as between a solid and a gas, produce strong ultrasound signals.

A typical human breast has a substantial number of features that are visualized with ultrasound. These features all have characteristic signals. Fibrous tissue or ligaments tend to show up as bright streaks, fat seems to appear as a dark gray area, the glandular tissue appears as a mottled medium gray mass. Cancerous lesions typically appear as a darker area with a rough outer edge that has reduced through transmission of the ultrasound energy.

However, due to the large amount of fibrous tissue normally present in a human breast, and due to the presence of ligaments running through the breast, a marker that simply has a bright signal alone will not provide a useful signal that can is readily discernable from the many anatomic features normally present within a human breast. Such markers are typically small, being sized to fit within a syringe or other delivery tube, and so are often not readily distinguishable from natural features of the breast, which include occasional small ultrasound-bright spots. Thus, it is generally desirable for an ultrasound-detectable biopsy marker material to provide an ultrasound signal which can be readily differentiated from anatomic structures within the breast, so that the identification and marking of a biopsy cavity does not require extensive training and experience.

A permanent metal or hard plastic, such as a permanent, biocompatible plastic, or other suitable permanent marker element may be left at a biopsy site at the completion of a biopsy if the site is to be located again in the future. Suture and collagen-based markers are not considered ideal materials for use as markers because they are hyperechoic, i.e., difficult to see under ultrasound because such materials are easily confused with other shadowing normal structures in the body such as fibrous tissue, fatty tissue, ducts in breast tissue, and the like, for example. Such tissue provides a background clutter that masks the presence of a marker made of metal, hard plastic, or other hyperechoic material.

Water, unlike metal, hard plastic, and other hyperechoic materials, is hypoechoic, i.e., easy to see under imaging techniques such as ultrasound. Therefore, it can be advantageous if a marker made of a hyperechoic material such as metal or hard plastic could be surrounded by an easily seen quantity of water. A hydrogel that has absorbed fluid from surrounding tissue provides such desirable ultrasound characteristics. The marker would become hydrated by natural body moisture after being positioned at a biopsy site, thereby surrounding the marker element with water. The water would be easily seen under ultrasound and therefore the marker element it surrounds would be easy to see.

The hydration of the marker material (122) of carrier (120) by the natural moisture of the tissue surrounding it causes expansion of the polymer and thus minimizes the risk of migration. The growing hydrogel based marker material (122) centers marker (100) in the biopsy cavity as it grows. As the hydrogel expands, naturally-present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame marker element (12). The hypoechoic nature of the hydrated marker material (122) enables ultrasound visibility of the marker element (12) within the hydrogel hydrated marker material (122) because the marker element (12) is outlined as a specular reflector within a hypoechoic hydrated marker having a water-like nonreflective substrate.

Marker material (122) can be further enhanced by forming air cavities or bubbles within the hydrogel that reflect under ultrasound imaging in a way that differs from the reflection of the hydrogel, making it easier to detect the hydrogel marker material (122). Such air cavities in the enhanced hydrogel are hypoechoic and thus serve to further indicate the location of marker (100). Previously incorporated by reference, U.S. Pat. No. 8,939,910, gives an example of creating air cavities using inserts of differing sizes and shapes. The inserts are placed in the hydrogel during the manufacturing process and removed from the hydrogel after it is cured to leave air-filled cavities in the hydrogel marker. The air-filled cavities image differently under ultrasound than the reflection of the hydrogel and allow the marker to be more easily detected. However, biopsy markers are typically very small, and it can be challenging to use inserts in manufacturing biopsy markers. For example, it can be difficult to remove the inserts from the cured hydrogel.

Aspects presented herein provide a method and system for enhancing a marker material, such as a hydrogel to form air bubbles in the hydrogel material using at least two electronic fluid dispensers (EFDs). The EFDs may be connected to or coupled to an apparatus having two portions. The EFDs may be driven in a way that cycles the hydrogel material back and forth between the two portions of the apparatus in order to form air bubbles in the hydrogel. The hydrogel, enhanced with the air bubbles, can then be formed into markers. The enhanced hydrogel may be cured, dehydrated, etc. as part of the preparation of the marker.

Aspects presented herein provide a consistent speed and pressure for moving marker material (122) between the two containers. This provides a more consistent, reliable mixture of air bubbles into marker material (122). The consistent mixture of air bubbles helps with the hydration of the marker material (122) when it is placed at a biopsy site.

Figure 2:
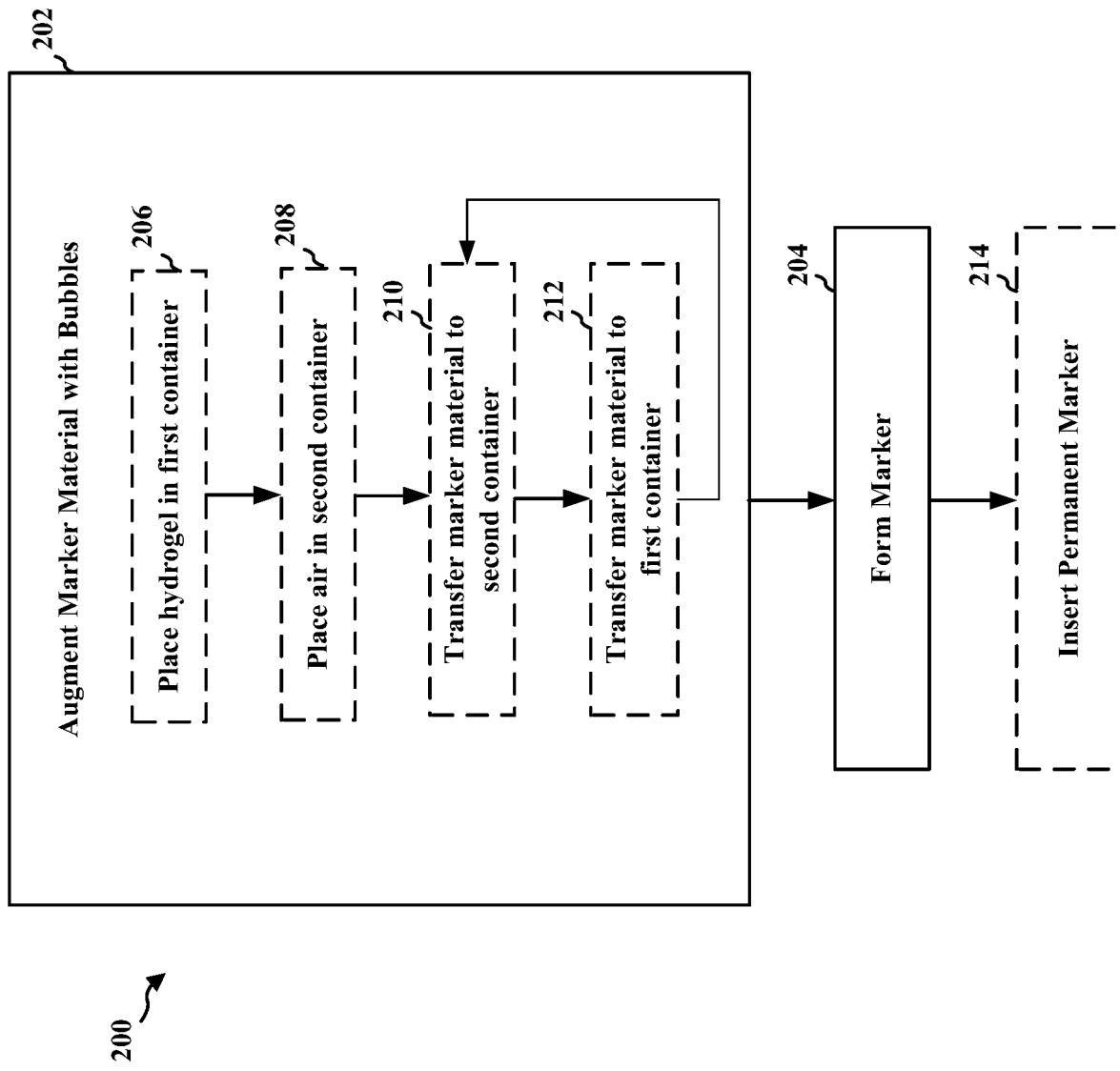
FIG. 2 illustrates an example method of manufacturing a marker comprising enhancing a marker material to include a plurality of air bubbles, in accordance with aspects of the present disclosure.

FIG. 2 illustrates a flow chart of an example method (200) of manufacturing a marker, such as marker (100) described above. The method may be performed, for example, using an aeration system such as systems (300, 500, 600) described below. The steps in FIG. 2 that are illustrated using a dashed line may optionally be repeated multiple times. At item (202), a marker material similar to marker material (122) described above is enhanced to include a plurality of air bubbles, or air cavities, using at least a first EFD and a second EFD. Then, at item (204), a marker is formed using the enhanced marker material (122). As described above, marker material (122) may comprise a bioabsorbable material such as a hydrogel.

Enhancing marker material (122) at item (202) includes cycling repeatedly through a transfer process between a first container and a second container. For example, the transfer process may include transferring marker material (122) from the first container to the second container using the first EFD at item (210). Then, marker material (122) may then be returned to the first container by transferring marker material (122) from the second container back to the first container using the second EFD at item (212). As illustrated in FIG. 2, marker material (122) may be repeatedly transferred back and forth between the two containers by alternately driving the two EFDs. This cycle may automatically continue for a predetermined number of transfers and stop. Alternately, the cycle may continue until an operator stops the cycle.

Figure 3:
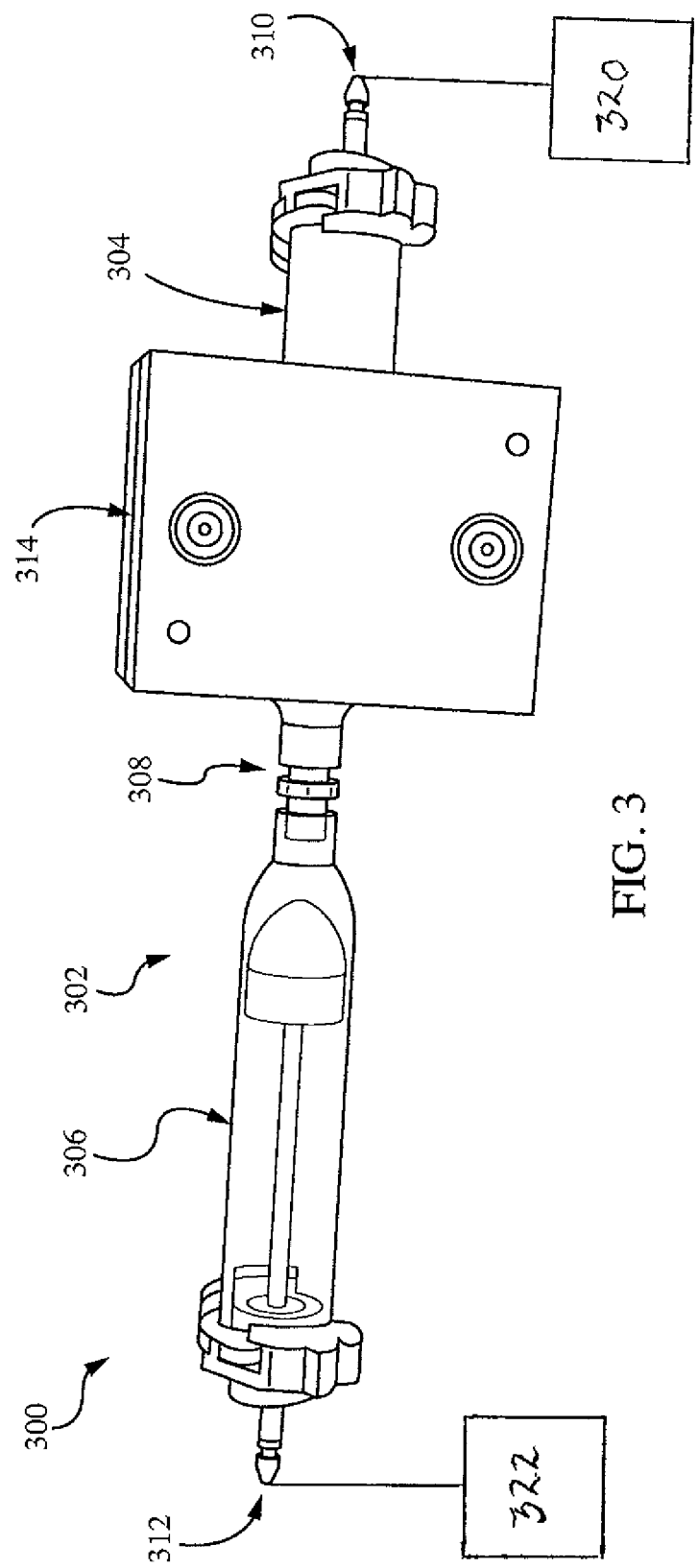
FIGS. 3 and 4 illustrate an example system for enhancing a marker material to include a plurality of air bubbles, in accordance with aspects of the present disclosure.

In one example, as best seen in FIG. 3, the first container may comprise a first syringe similar to container (304), described below. Similarly, the second container may comprise a second syringe similar to container (306), described below. The method may include placing marker material (122) in the first container, e.g., the first syringe, at item (206) and placing a selected amount of air in the second container, e.g., the second syringe, at item (208) and then beginning the transfer process cycle(s) between item (210) and item (212) using the two EFDs. In some examples, the transfer cycle may be driven manually by an operator activating each EFD independently. Alternatively, in other examples the transfer cycle may be driven automatically by control circuitry or processor coupled to each EFD. Thus, the transfer process may include a predetermined number of cycles that are performed manually or automatically that cycles between driving the first EFD and the second EFD. In another example, the transfer process may cycle automatically until it is stopped manually. This may allow an operator to visually determine when an appropriate amount of air bubbles have been formed in marker material (122).

After performing the steps illustrated within item (202) for a desired number of cycles, an inspection of the aerated marker material (122) may be made. If an additional amount of air bubbles is desired, the cycle of the steps illustrated by item (210) to item (212) may be repeated. The repeat may include a reduced number of cycles from the original transfer process or may include the same number of cycles as the original transfer process.

Once a desired amount of aeration has been obtained within marker material (122) using the step illustrated by item (210) to item (212), marker material (122) may be used to form carrier (120) of marker (122) as illustrated by item (204). During this step, aerated marker material (122) is injected into a plurality of smaller containers defining an approximate pill-shaped form. Once injected therein, marker material (122) may be cured or partially cured using light.

As illustrated at item (214), the method may further include inserting one or more marker elements (12) into the formed marker (100). During this step, marker element (12) can be inserted into the carrier (120) formed by marker material (122) using a manipulator such as a rigid wire, tube, and/or etc. The manipulator may then be extracted from marker material (122) after placement of marker element (12) within marker material (122).

After the marker (100) is formed at item (204), the marker (100) may be cured and/or dehydrated, as additional aspects of the manufacturing process. In examples where marker material (122) is hydrogel, the curing process may be performed by applying light of various wavelengths to the marker (100). Light may be applied until marker material (122) is fully cured. In some examples, light may be applied for a limited period to partially cure marker material (122). In the partially cured state, marker material (122) may be cured to substantially fix marker element (12) within marker material (122) as described above in connection with item (214). At the same time, the curing of marker material (122) may be substantially limited to permit extraction of manipulators or other support structures related to placing marker element (12) within marker material (122). Once such structures are removed, light may be applied again to fully cure marker material (122).

FIG. 3 illustrates an exemplary system (300) for enhancing a marker material (122) biopsy marker (100), described above. System (300) may be used to perform aspects of the method described above with respect to FIG. 2. As will be described in greater detail below, system (300) includes a transfer apparatus (302) that is generally configured to transfer a fluid medium (e.g., uncured marker material (122)) between two discrete containers (304, 306) to provide aeration to the fluid medium.

As seen in FIG. 3, the transfer apparatus (302) includes a first container (304) and a second container (306) each having a connector at its distal end such as a male luer connector. Containers (304, 306) are detachably coupled to each other at a connection (308). In the present example, connection (308) includes a standard luer connector (e.g., a female-female coupler that couples together the male luer connectors of containers (304, 306)), available from Cole-Parmer and other companies, such that containers (304, 306) are axially rotatable relative to each other to permit selective coupling and decoupling. In other examples, any suitable connector may be included in connection (308). For instance, in some examples each container (304, 306) may include a barbed or cylindrical tip such that each connector may be coupled to the other by a flexible tube with an interference fit with each barbed tip. In still other examples, container (304, 306) may include any other suitable connector as will be apparent to those of ordinary skill in the art in view of the teachings herein. In yet other examples, connection (308) may be omitted entirely. For instance, in an alternate example, transfer apparatus (302) can be a single container having two separate portions connected by a fluid lumen or other passageway.

In the example in FIG. 3, first container (304) comprises a syringe, and second container (306) comprises another syringe. The syringes may be selected to both be a dark color or alternatively to both be clear and colorless or one syringe could be a dark color and the other could be clear and colorless. Whether a given syringe is clear, colorless, dark colored, or otherwise, such a syringe may be coated and/or impregnated with materials to block certain specific wavelengths of light. As will be understood, each syringe is generally used in connection with marker material (122). As described above, in some versions marker material (122) is cured using light. Thus, it may be beneficial for each syringe to have light blocking properties to prevent unintended curing of marker material (122). In syringes that are darker or opaque in character, light blocking properties may be inherent. However, in other syringes, additional materials may be required to provide light blocking properties. In still other examples, each syringe may not itself have light blocking properties. Instead, an opaque sheath or other similar structure may be fitted over each syringe to prevent light from entering syringe. By way of example only, in some examples such a sheath can be formed by modifying a standard latex or non-latex exam glove. Of course, other suitable sheaths may be apparent to those of ordinary skill in the art in view of the teachings herein.

Transfer apparatus (302) is generally configured to receive to marker material (122) described above and a selected amount of air. For example, unaerated and uncured marker material (122) may be placed in first container (304), and a selected amount of air may be placed in second container (306). Each container (304, 306) may then be alternatingly actuated as described below to transfer the combination of air and uncured marker material (122) between each container to aerate marker material (122).

A first EFD (320) may be coupled to an EFD connection (310) fastened to an open end (402) of first container (304). A second EFD (322) may be coupled to an EFD connection (312) fastened to an open end (404) second container (306). Each EFD (320, 322) is generally configured to provide a precise pulse of pressurized fluid to each container (304, 306) to transfer marker material (122) between containers (304, 306). Although transfer apparatus (302) of the present example is shown as being used with an EFD (320, 322) for each container (304, 306), it should be understood that in other examples only a single EFD may be used with one container (304, 306), while another container (306, 304) may be manually actuated by an operator. In other examples, both EFDs (320, 322) may be omitted entirely. Instead, one or both EFDs may be replaced with an alternative actuation mechanism such as a solenoid, linear actuator, rotary piston driver, or any other suitable mechanism.

Figure 4:
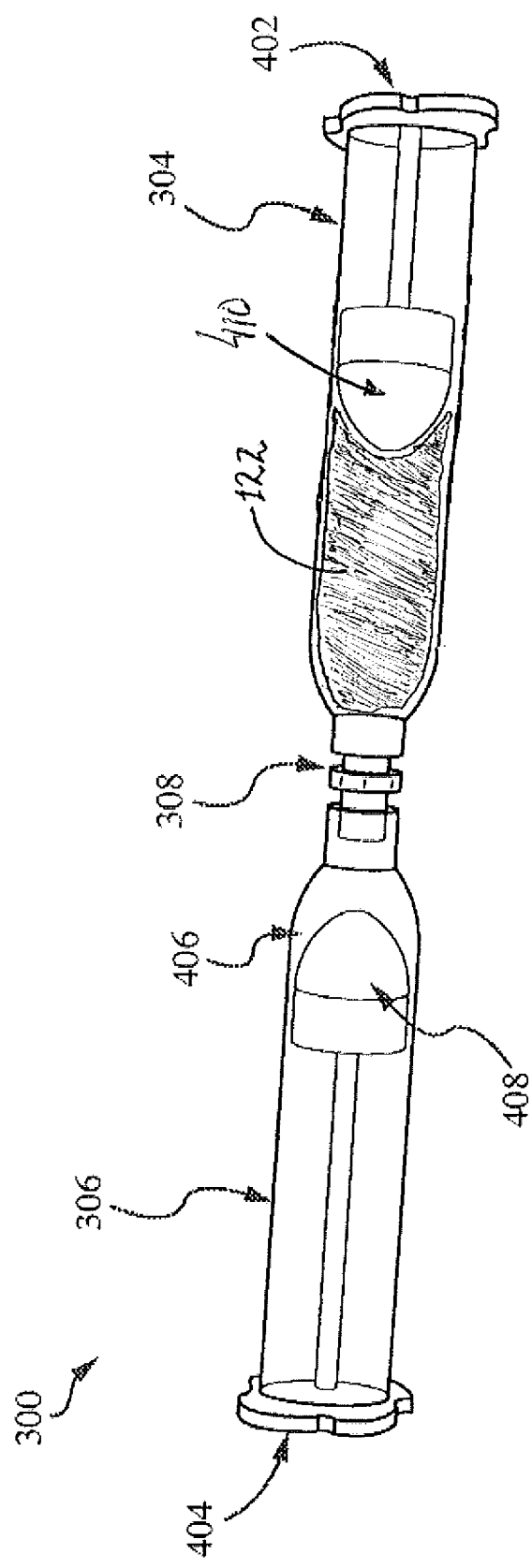

FIG. 4 illustrates system (300) with EFD connections (310, 312) removed so that the open ends (402, 404) of the containers (304, 306) are visible. For example, the first end of the transfer apparatus comprises an open end (402) and the second end of the transfer apparatus comprises an open end (404), opposite open end (402). Each EFD connection (310, 312) is configured to releasably secured to each open end (402, 404) of first container (304) and second container (306), respectively. This configuration generally permits each container (304, 306) to be opened for insertion of marker material (122) and/or atmospheric air. In the present example, each EFD connection (310, 312) is configured to secure to a corresponding flange protruding outwardly from each container (304, 306) adjacent to each open end (402, 404). However, it should be understood that in other examples each EFD connection (310, 312) may be configured to couple to each container (304, 306) in numerous other ways as will be apparent to those of ordinary skill in the art in view of the teachings herein.

FIG. 4 illustrates an amount of air (406) within second container (306) and an amount of marker material (122) within first container (304). A plunger (408) maintains the air (406) within second container (306), while another plunger (410) maintains marker material (122) within first container (304). For example, about 10 cc of marker material (122) (e.g., hydrogel) is maintained within first container (304). Within second container (306), the selected amount of air (406) may comprise an amount between about 1 cc and about 3 cc, e.g., approximately 2 cc of air. In examples using alternative quantities of marker material (122), a ratio of 5:1 marker material (122) to air may generally be maintained.

FIG. 3 also illustrates a support component (314) configured to hold the transfer apparatus (302) in a fixed position. Support component (314) is generally configured to receive first container (304) or second container (306) to secure transfer apparatus (302) relative to a fixed reference point. As will be described in greater detail below, in some examples support component (314) is itself fixed to a fixture or other components to secure the position of support component (314).

Figure 5:
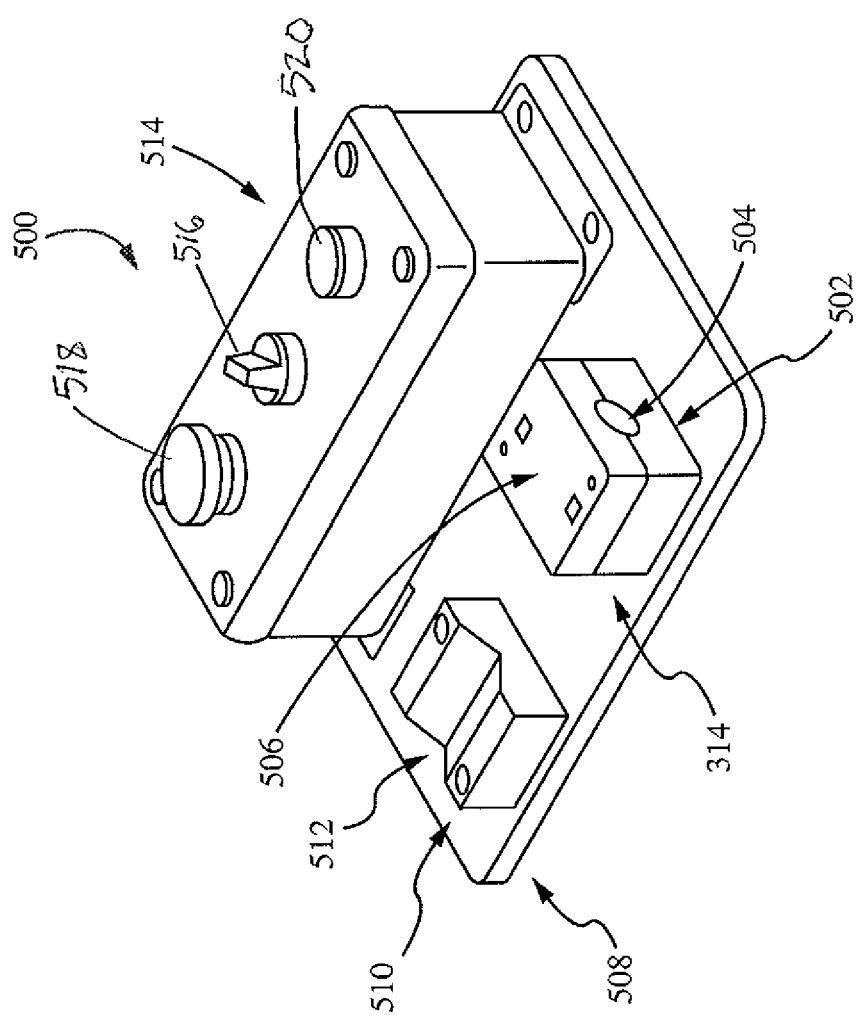
FIG. 5 illustrates an example system for enhancing a marker material to include a plurality of air bubbles, in accordance with aspects of the present disclosure.

FIG. 5 illustrates an exemplary fixation system (500) for enhancing a marker material such as a marker material (122) described above. System (500) of the present example is generally readily usable with certain elements of system (300) described above. For instance, as illustrated in FIG. 3 and described above, support component (314) of system (300) may be configured to surround at least a portion of transfer apparatus (302). By way of example only, support component (314) surrounds a portion of first container (304). Support component (314) may include a first portion (502) configured to receive the portion of the transfer apparatus in a groove (504) or shaped surface. The support component (314) in FIG. 5 also includes a second portion (506) that holds the transfer apparatus in a supported position together with first portion (502). The two portions (502) and (506) may be configured to fit against or clamp the transfer apparatus (302) between the two portions (502, 506). In some examples, portions (502, 506) are selectively coupled together using a screw, a latch, a snap, etc. so that the transfer apparatus (302) can be held securely in the support component (314) and then removed after the bubbles have been formed in the marker material.

FIG. 5 illustrates that support component (314) may be coupled to a support surface (508). A second support component (510) may also be coupled to the support surface (508) and may be configured to receive s second portion of the transfer apparatus (302). For example, the second support component (510) may be configured to receive a portion of the second container (306) within a groove (512). Although not illustrated, the second support component (510) may also include an upper portion that clamps around the transfer apparatus, similar to the upper portion (506) of support component (314). Alternately, the second support component (510) might include only the illustrated portion. Second support component (510) might only partially surround the transfer container (302), because the first support component (314) already clamps around the transfer apparatus (302) and keeps it in a relatively fixed position.

System (500) of the present example further includes a controller (514) that is generally in communication with each EFD (320, 322) to controls the transfer process between each container (304, 306) of transfer container (302) via each EFD (320, 322). Controller (514) in the present example is coupled to support surface (508). However, in other examples controller (514) is situated separately from the support surface (508) to provide remote operation of each EFD (320, 322).

Controller (514) includes a power switch (516), a restart button (518), and a return switch (520) for operating system (300) via each EFD (320, 322). In the present example, power switch (516) of controller (514) is useable for turning system (300) on and beginning the transfer process that cycles the marker material (122) and air between the two portions of the transfer apparatus (302). By actuating restart button (518) and/or return switch (520), system (300) may perform a predetermined number of cycles between containers (304, 306) of the transfer apparatus (302). In another example, the cycles may continue until the operator turns the system off by actuating power switch (516) of controller (514). At the end of the transfer process, it may be desirable to have the enhanced marker material (122) in one portion of the transfer apparatus (302), e.g., in one container (304, 306). Therefore, one of the buttons or switches on controller (514) may operate one of the EFDs (320, 322) to transfer the enhanced marker material to a desired container (304, 306).

Although controller (514) of the present example is shown has having a certain operator interface, it should be understood that in other examples controller (514) may have any other suitable operator interface configuration. For instance, in some examples controller (514) includes a single button or selector switch for activating a transfer cycle. In addition or in the alternative, in some examples controller (514) also includes various visual or auditory indicators such as LEDs, speakers, bells, buzzers, and/or etc. to provide status information to an operator. In still other examples, any other suitable operator interface configuration may be used as will be apparent to those of ordinary skill in the art in view of the teachings herein.

Figure 6:
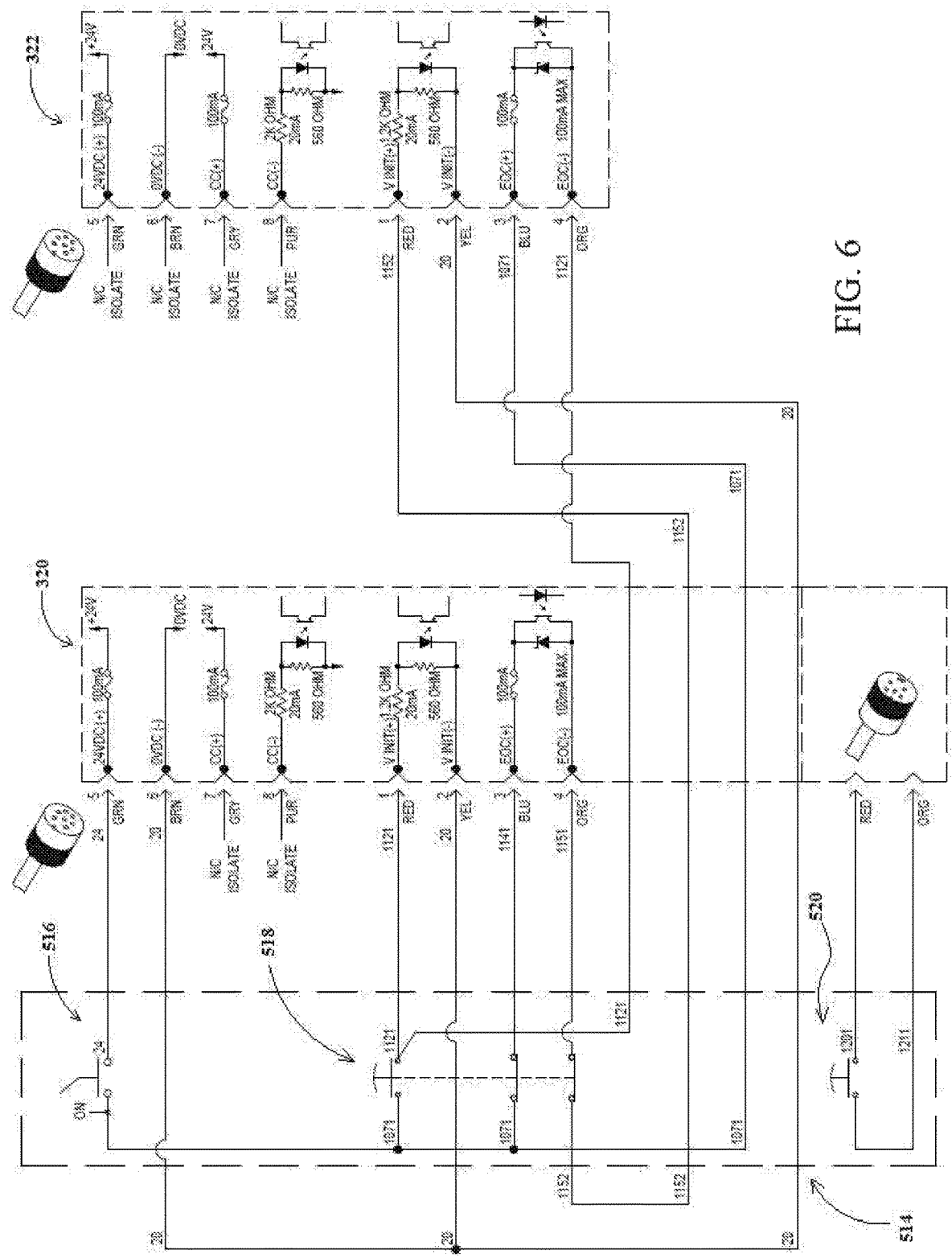
FIG. 6 illustrates an example of EFD connections, in accordance with aspects of the present disclosure.

FIG. 6 illustrates an exemplary schematic for connections that can be made between each EFD (320, 322) and controller (514) to facilitate performance of the transfer cycle. As can be seen, each EFD (320, 322) generally includes a multi-signal input/output connector (321, 323). Each connector (321, 323) includes a plurality of interfaces that permit communication between controller (514) and each EFD (320, 322). Although not shown, it should be understood that each EFD (320, 322) is generally equipped with various internal control elements such as relays, control logics, switches, integrated circuits, and/or etc. Through these internal control elements, each EFD (320, 322) may be responsive to the receipt of one or more external signals. Upon receipt of one or more external signals, a selected EFD (320, 322) is configured to activate for a predetermined period of time, thereby suppling a pressurized medium to transfer apparatus (302). Once the predetermined period of time has elapsed, the various internal control elements of each EFD (320, 322) are configured to supply an internal signal externally via connector (321, 323). As will be described in greater detail below, this internal signal is generally communicated externally to coordinate operation with another EFD (320, 323) or other elements associated with system (300) (e.g., indicators if equipped).

As can be seen in FIG. 6, one terminal of power switch (516) is coupled to EFD (320) via lead (24). Another terminal of power switch (516) is coupled to both EFD (322) and two terminals of restart button (518) of controller (514) via lead (1071). This configuration generally permits power switch (516) to energize lead (1071) with a voltage. In the present example, 24 volts DC is used, although other voltages may be used. As will be described in greater detail below, this configuration generally permits restart button (518) to be used to initiate a variety of operations such as starting a cycle and/or restarting a cycle.

In the present example, power switch (516) is configured as a two-position selector switch. Thus, power switch (516) is configured to transition between an open position and a closed position. Once disposed in either the open position or the closed position, power switch (516) will remain in such a position until an operator desires to transition power switch (516) to another position. When power switch (516) is in the open position, an open circuit condition occurs such that lead (1071) is not in communication with lead (24). This results in lead (1071) having no voltage supplied via lead (24). By contrast, when power switch (516) is in the closed positon, a closed-circuit condition occurs such that lead (1071) is in communication with lead (24). This results in lead (1071) being energized with a voltage via lead (24). As will be described in greater detail below, this voltage may be used in connection with restart button (518) to initiate a variety of operations.

As described above, two terminals of restart button (518) are in communication with lead (1071), which is also in communication with power switch (516) and EFD (322). Of the two terminals of restart button (518) that are in communication with lead (1071), one terminal is opposite to another terminal that is in communication with lead (1121). Lead (1121) is correspondingly in communication with EFD (320) and EFD (322). Still another terminal of restart button (518) is further coupled to EFD (320) via lead (1141). Yet another terminal of restart button (518) is connected to lead (1152), which is opposite of yet another terminal of restart button (518) that is in communication with lead (1151). Lead (1152) is in communication with EFD (322), while lead (1151) is in communication with EFD (320).

In the present example, restart button (518) is configured as a three-switch push button switch. Thus, as seen in FIG. 6, restart button (518) includes three switches. Restart button (518) is further configured to be transitioned between a first position and a second position, with restart button (518) being resiliently biased towards the first position. In the first position, one switch is in an open condition such that lead (1071) is not in communication with lead (1121). Another switch is in a closed position when restart button (518) is in the first position such that lead (1071) is in communication with lead (1141). Similarity, still another switch is in a closed position when restart button (518) is in the first position such that lead (1152) is in communication with lead (1151).

When restart button (518) is transitioned to the second position, switch coupled to lead (1071) and lead (1121) is transitioned to a closed position, thereby placing lead (1071) and lead (1121) into communication with each other. By contrast, when restart button (518) is transitioned to the second position, switch coupled to lead (1071) and lead (1141) is transitioned to an open position, thereby placing lead (1071) out of communication with lead (1141). Also in the second position, switch coupled to lead (1152) and lead (1151) is transitioned to an open position, thereby placing lead (1152) out of communication with lead (1151). As will be described in greater detail below, this configuration is generally configured to shift voltage supplied by power switch (516) to different circuits to thereby activate and/or deactivate different modes of operation.

One terminal of return switch (520) of controller (514) is in communication with a portion of control circuitry of EFD (320) via lead (1201). Another terminal of cycle selector switch (520) is likewise in communication with another portion of control circuitry of EFD (320) via lead (1211). In the present example, leads (1201, 1211) are shown as coupling to control circuitry of EFD (320) that is relatively isolated relative to the rest of control circuitry of EFD (320). In other words, in the present example leads (1201, 1211) couple to a different connector of EFD (320). In some examples, leads (1201, 1211) may couple to a foot pedal connector of EFD (320) to access specific operational features of EFD (320). However, it should be understood that in other examples leads (1201, 1211) may couple to standard input/output features of EFD (320). As will be described in greater detail below, this configuration permits an operator to adjust certain operational parameters of each EFD (320, 322).

In the present example, return switch (520) is configured as a single-switch push button. Thus, return switch (520) is configured to transition between a first position and a second position, while be resiliently biased towards the first positon. As shown in FIG. 6, when return switch (520) is in the first position, a single switch of return switch (520) is in an open circuit condition. In this condition, lead (1201) is not in communication with lead (1211). By contrast, when return switch (520) is in the second position, the single switch of return switch (520) is in a closed-circuit condition. In this condition, lead (1201) is in communication with lead (1211). This completes a circuit with EFD (320) to activate certain operational features as will be described in greater detail below.

Lead (20) provides direct communication between each EFD (320, 322). This permits each EFD (320, 322) to transfer signals between each other. It should be understood that lead (20) only communicates with each EFD (320, 322). Thus, transitioning power switch (516), restart button (518), or return switch (520) has no effect on the state of lead (20). As will be described in greater detail below, this configuration permits one EFD (320, 322) to transition the other EFD (322, 320) under some circumstances.

In an exemplary use, each EFD (320, 322) is initially set with various operational parameters. Although each EFD (320, 322) can be programmed with different operational parameters, in the present use an operator can generally set both EFDs (320, 322) to use the same operational parameters. By way of example only, suitable operational perimeters may include a time setting of approximately 0.82 seconds and a pressure setting of approximately 31.5 psi. Of course, in other examples, various alternative time and pressure settings may be used.

Once each EFD (320, 322) has been set with suitable operational parameters, an operator may initiate an aeration cycle. To initiate the aeration cycle, an operator may hold reset button (518) in the second position while actuating power switch (516) from an "off" position to an "on" position. Once power switch (516) is actuated to the on position, a closed circuit is created that permits voltage to flow from lead (24) to lead (1071). Simultaneously, while reset button (518) is being held in the second position, lead (1071) is in communication with lead (1121). Correspondingly, lead (1071) is not in communication with lead (1141) and lead (1152) is not in communication with lead (1151).

This configuration results in voltage being applied to lead (1121) via lead (1071). This completes an internal circuit within both EFD (320) and EFD (322) via lead (1121) and lead (20). In EFD (320) an initiate cycle circuit is completed, which is used by the internal circuitry of EFD (320) to initiate a cycle. Simultaneously, an end of cycle circuit is completed within EFD (322), which is used by the internal circuitry of EFD (322) to transition to a waiting state where EFD is waiting for further input.

Once a cycle has been initiated by EFD (320), an operator releases reset button (518) and EFD (320) automatically applies a predetermined amount of pressure to container (304) for a predetermined duration of time. At the conclusion of the predetermined duration of time, EFD (320) stops supplying the predetermined amount of pressure to container (304).

After EFD (320) has completed a cycle, EFD (320) automatically generates a pulse by completing an end of cycle circuit between lead (1141) and lead (1151). Because result button (518) was previously released, lead (1141) is in communication with lead (1071), which is in communication with lead (24) via power switch (516). Correspondingly, lead (1151) is in communication with lead (1152). Lead (1152) is in communication with EFD (322). Accordingly, voltage is suppled from lead (24) to lead (1152) via leads (1071, 1141, 1151). This completes an initiate cycle circuit within EFD (322) via lead (20). As a result, internal circuitry of EFD (322) is responsive to the initiate cycle circuit to automatically initiate a cycle. Thus, on a general level, once EFD (320) completes a cycle, EFD (320) automatically sends a signal to EFD (322) that the cycle is complete. This signal is in turn activates EFD (322) to perform a cycle while EFD (320) waits for further input.

Once a cycle has been initiated by EFD (322), EFD (322) automatically applies a predetermined amount of pressure to container (306) for a predetermined duration of time. At the conclusion of the predetermined duration of time, EFD (322) stops supplying the predetermined amount of pressure to container (306). As with EFD (320) described above, EFD (322) next automatically generates a pulse by completing an end of cycle circuit between lead (1071) and lead (1121). This pulse travels through lead (1121), which is also in communication with EFD (320). This completes an initiate cycle circuit within EFD (320) via lead (20). As a result, internal circuitry of EFD (320) is responsive to the initiate cycle circuit to automatically initiate another cycle while EFD (322) waits for further input. Thus, on a general level, once EFD (322) completes a cycle, EFD (322) automatically sends a signal to EFD (320) that the cycle is complete. This signal is in turn activates EFD (320) to perform a cycle while EFD (322) waits for further input.

The process of each EFD (320, 322) communicating with the other EFD (322, 320) to alternatingly perform cycles is repeated as described above for a total of approximately 10 to 15 cycles or in some cases as many as 30 cycles. It should be understood, during each cycle the combination of air and marker material (122) is transferred from container (304) to container (306) or from container (306) to container (304), depending on which EFD (320, 322) is in cycle. In some examples, each EFD (320, 322) includes an onboard counter to automatically stop cycling after a predetermined number of cycles. Alternatively, in other examples each EFD (320, 322) is configured to cycle indefinitely until an operator intervenes to stop both EFDs (320, 322).

Figure 7A:
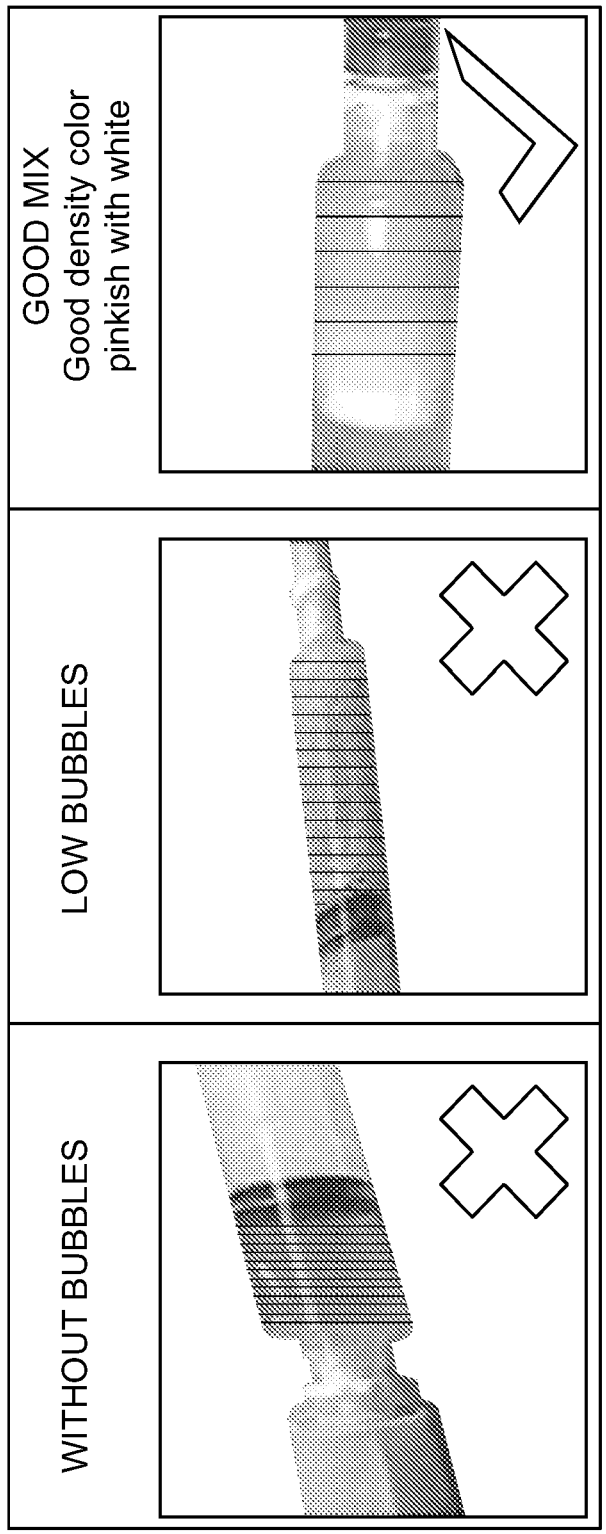
FIGS. 7A and 7B illustrate an example of visually inspecting the enhanced marker material, in accordance with aspects of the present disclosure.
Figure 7B:
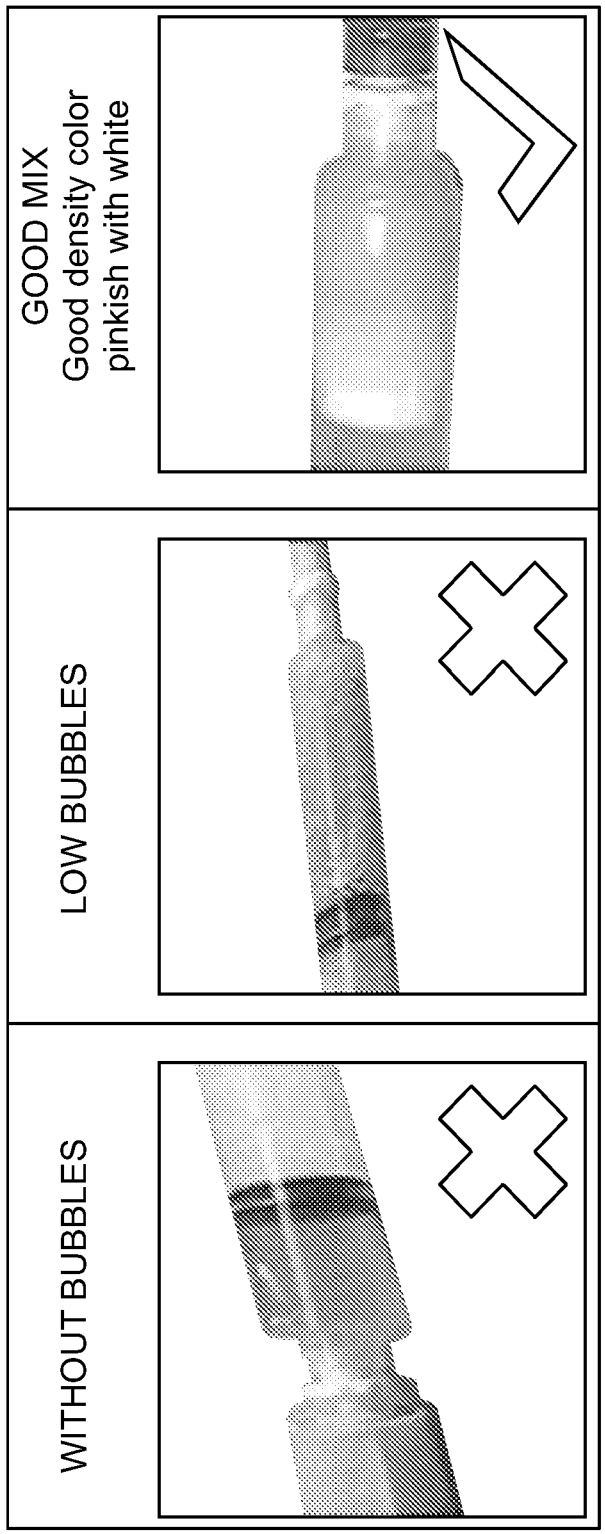

Regardless of whether each EFD (320, 322) is configured to cycle indefinitely or for a predetermined number of cycles, it should be understood that controller (514) is generally configured to stop each EFD (320, 322) after any number of cycles. This may be desirable to permit an operator to obtain a specifically desired amount of aeration in marker material (122). For instance, an operator may continuously monitor marker material (122) as it is transferred between containers (304, 306). Based on the visual appearance of marker material (122), an operator may then stop each EFD (320, 322) as desired for either further inspection or to use marker material (122) for forming a marker (100). An acceptable mixture of air into a hydrogel marker material may have a discernible (pinkish) color contrasting with (white) air bubbles, as illustrated in FIGS. 7A and 7B. The bubbles may be visible in the enhanced marker material. FIG. 7A illustrates a black and white drawing showing the change in the hydrogel to include bubbles, and FIG. 7B is a photo illustration of the visible change in the hydrogel. Although the present example involves using visual inspection to detect the level of aeration in marker material (122), it should be understood that in other examples alternative methods of inspection may be used. For instance, in some examples an optical sensor can be positioned adjacent to container (304) and/or container (306). The light sensor may be configured to measure the amount of light passing through marker material (122). If the level of light passing through marker material (122) is detected by the light sensor to be below a predetermined threshold value, then the light sensor may communicate with other circuitry to provide an indication of sufficient aeration (e.g., light, tone). In some examples using the light sensor, such a light sensor may also be in communication with controller (514). In such examples, controller (514) may include additional circuitry to automatically stop each EFD (320, 322) after the light sensor has detected a sufficient amount of aeration.

An operator may stop EFDs (320, 322) from cycling using power switch (516). For instance, an operator may stop each EFD (320, 322) by moving power switch (516) to the "off" position. In this position, lead (24) is not in communication with lead (1071). Thus, voltage is not supplied to lead (1071) via lead (24). In the absence of voltage via lead (24), lead (1071) cannot be used to communicate pulses between each EFD (320, 322) that signal when a cycle has completed. Thus, each EFD (320, 322) transitions to a waiting state when power switch (516) is switched to the "off" position.

In some instances, it may be desirable to return the combination of air and marker material (122) to a particular container (304, 306) after an operator has transitioned power switch (516) to the "off" position. In the present example, controller (514). Is configured to return the combination of air and marker material (122) to container (306) after an operator presses and holds return switch (520). For instance, pressing return switch (520) completes a circuit between lead (1201) and lead (1211). Lead (1201) and lead (122) are both in communication with internal circuitry of EFD (320). The internal circuitry of EFD (320) is responsive to the circuit completed by return switch (520) to activate EFD (320) at a predetermined amount of pressure for as long as the circuit is completed by return switch (520). Thus, as return switch (520) is held, EFD (320) supplies pressure to container (304). This causes container (304) to transfer its contents to container (306). Once the combination of air and marker material (122) has fully transferred to container (306), an operator may release return switch (520) to complete the aeration procedure.

Although manual buttons are shown in connection with the present example, it should be understood that in some examples a user interface at a display screen or computer may also be used to operate system (300). For example, the system may further comprise memory and at least one processor coupled to the memory. The processor may be configured to cycle each EFD (320, 322) through a repeated transfer process. The repeated transfer process may include transferring the marker material (122) from one container (304, 306) of the transfer apparatus (302) to another container (306, 304) of transfer apparatus (302) using a corresponding EFD (320, 322).

Figure 8:
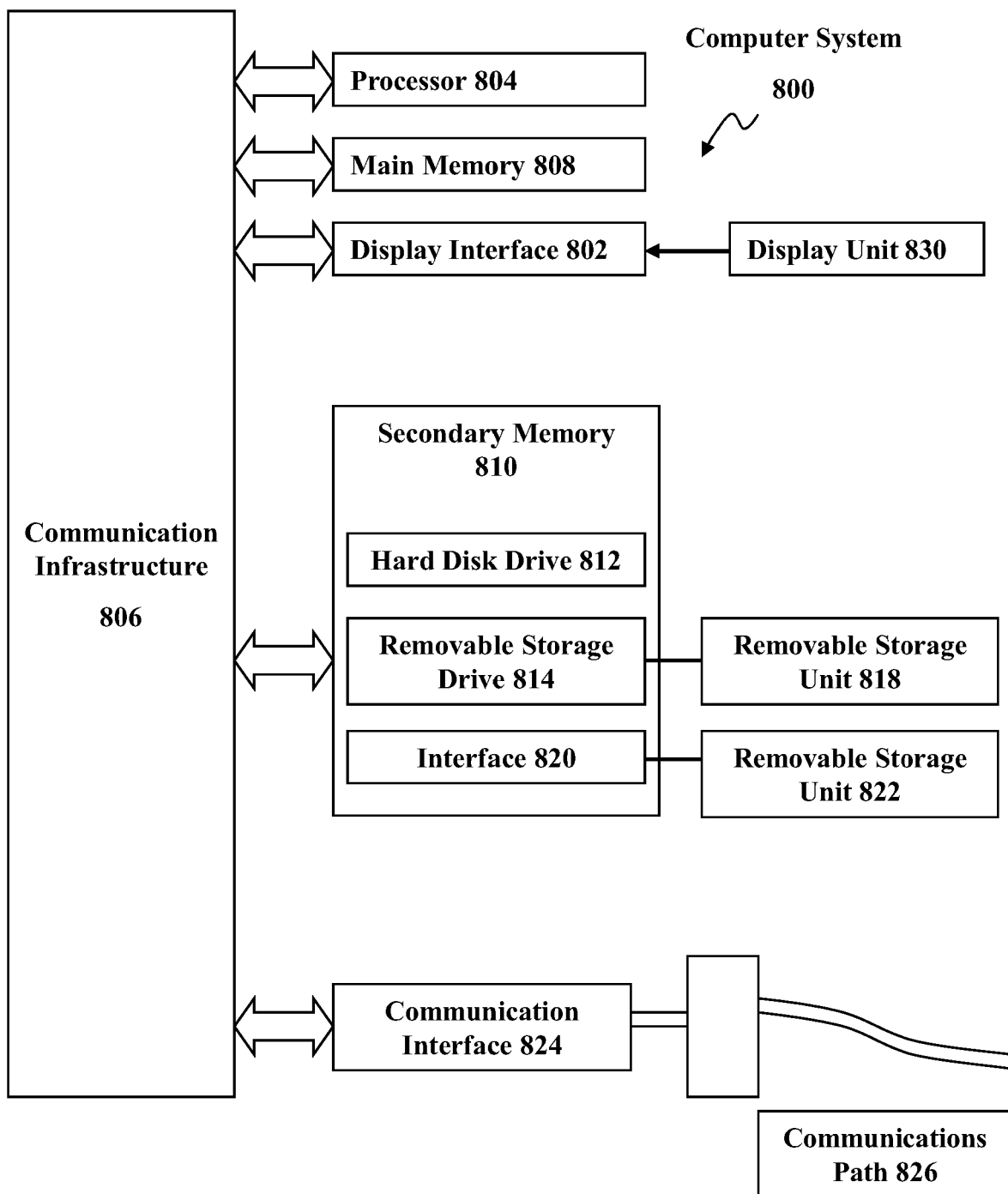
FIG. 8 illustrates an example system diagram of various hardware components and other features, for use in accordance with aspects of the present disclosure.

FIG. 8 presents an example system diagram of various hardware components and other features, for use in accordance with aspects presented herein. The aspects may be implemented using hardware, software, or a combination thereof and may be implemented in one or more computer systems or other processing systems. In one example, the aspects may include one or more computer systems capable of carrying out the functionality described herein, for example aspects described in connection with FIG. 2, e.g., items 202, 210, 212, etc. An example of such a computer system (800) is shown in FIG. 8.

Computer system (800) includes one or more processors, such as processor (804).

The processor (804) is connected to a communication infrastructure (806) (e.g., a communications bus, cross-over bar, or network). Various software aspects are described in terms of this example computer system. After reading this description, it will become apparent to a person skilled in the relevant art(s) how to implement the aspects presented herein using other computer systems and/or architectures.

Computer system (800) can include a display interface (802) that forwards graphics, text, and other data from the communication infrastructure (806) (or from a frame buffer not shown) for display on a display unit (830). Computer system (800) also includes a main memory (808), preferably random access memory (RAM), and may also include a secondary memory (810). Secondary memory (810) may include, for example, a hard disk drive (812) and/or a removable storage drive (814), representing a floppy disk drive, a magnetic tape drive, an optical disk drive, etc. Removable storage drive (814) reads from and/or writes to a removable storage unit (818) in a well-known manner. Removable storage unit (818), represents a floppy disk, magnetic tape, optical disk, etc., which is read by and written to removable storage drive (814). As will be appreciated, the removable storage unit (818) includes a computer usable storage medium having stored therein computer software and/or data.

In alternative aspects, secondary memory (810) may include other similar devices for allowing computer programs or other instructions to be loaded into computer system (800). Such devices may include, for example, a removable storage unit (822) and an interface (820). Examples of such may include a program cartridge and cartridge interface (such as that found in video game devices), a removable memory chip (such as an erasable programmable read only memory (EPROM), or programmable read only memory (PROM)) and associated socket, and other removable storage units (822) and interfaces (820), which allow software and data to be transferred from the removable storage unit (822) to computer system (800).

Computer system (800) may also include a communications interface (824).

Communications interface (824) allows software and data to be transferred between computer system 800 and external devices. For instance, in some examples communication interface (824) is in communication with one or more EFDs (320, 322). In still other examples, computer system (800) may be fully or partially integrated into one or more EFDs (320, 322) such that communication interface (824) is disposed entirely within the one or more EFDs (320, 322).

Examples of communications interface (824) may include a modem, a network interface (such as an Ethernet card), a communications port, a Personal Computer Memory Card International Association (PCMCIA) slot and card, etc. Software and data transferred via communications interface (824) are in the form of signals, which may be electronic, electromagnetic, optical or other signals capable of being received by communications interface (824). These signals are provided to communications interface (824) via a communications path (e.g., channel) (826). This path (826) carries signals and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive (880), a hard disk installed in hard disk drive (870), and signals. These computer program products provide software to the computer system (800). Aspects presented herein may include such computer program products.

Computer programs (also referred to as computer control logic) are stored in main memory (808) and/or secondary memory (810). Computer programs may also be received via communications interface (824). Such computer programs, when executed, enable the computer system (800) to perform the features presented herein, as discussed herein. In particular, the computer programs, when executed, enable the processor (810) to perform the features presented herein. Accordingly, such computer programs represent controllers of the computer system (800).

In aspects implemented using software, the software may be stored in a computer program product and loaded into computer system (800) using removable storage drive (814), hard drive (812), or communications interface (820). The control logic (software), when executed by the processor (804), causes the processor (804) to perform the functions as described herein. In another example, aspects may be implemented primarily in hardware using, for example, hardware components, such as application specific integrated circuits (ASICs). Implementation of the hardware state machine so as to perform the functions described herein will be apparent to persons skilled in the relevant art(s).

In yet another example, aspects presented herein may be implemented using a combination of both hardware and software.

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing a marker comprising: enhancing a marker material to include a plurality of air bubbles using at least a first EFD and a second EFD; and forming a marker body using the enhanced marker material.

Example 2

The method of Example 1, wherein enhancing the marker material comprises cycling repeatedly through a transfer process between a first container and a second container, the transfer process comprising: transferring the marker material from the first container to the second container using the first EFD; and transferring the marker material from the second container back to the first container using the second EFD.

Example 3

The method of Example 2, wherein the first container comprises a first syringe and the second container comprises a second syringe, and wherein the marker material is placed in the first syringe and a selected amount of air is placed in the second syringe before the transfer process.

Example 4

The method of Example 1, wherein the marker material comprises a hydrogel.

Example 5

The method of Example 4, further comprising: inserting a radiopaque marker into the marker.

Example 6

A system for enhancing a marker material, the system comprising: a transfer apparatus configured to receive a marker material and a selected amount of air; a first EFD coupled to a first end of the transfer apparatus; and a second EFD coupled to a second end of the transfer apparatus.

Example 7

The system of Example 6, wherein the first end of the transfer apparatus comprises a first opening to which the first EFD is coupled and the second end of the transfer apparatus comprises a second opening opposite the first opening, the second EFD being coupled to the second opening.

Example 8

The system of any one or more of Examples 6 through 7, wherein the transfer apparatus comprises a first syringe coupled to a second syringe.

Example 9

The system of any one or more of Examples 6 through 8, further comprising a support component configured to hold the transfer apparatus in a fixed position.

Example 10

The system of any one or more of Examples 6 through 9, further comprising: memory; and at least one processor coupled to the memory and configured to: cycle the first EFD and the second EFD through a repeated transfer process comprising: transferring the marker material from a first portion of the transfer apparatus to a second portion of the transfer apparatus using the first EFD; and transferring the marker material from the second portion of the transfer apparatus back to the first portion of the transfer apparatus using the second EFD.

Example 11

A system for aerating a marker material, the system comprising: a transfer apparatus including a first portion and a second portion, wherein the first portion is in communication with the second portion to transfer at least the marker material between the first portion and the second portion; a first EFD, wherein the first EFD is in communication with the first portion of the transfer apparatus such that the first EFD is configured to selectively drive at least the marker material from the first portion to the second portion; a second EFD, wherein the second EFD is in communication with the second portion of the transfer apparatus such that the second EFD is configured to selectively drive at least a portion of the marker material from the second portion to the first portion; and a controller, wherein the controller is in communication with both of the first EFD and the second EFD to thereby coordinate operation of the first EFD and the second EFD.

Example 12

The system of Example 11, wherein the controller includes a first switch and a second switch, wherein the first switch is configured to communicate with at least the first EFD to initiate an aeration cycle.

Example 13

The system of Example 12, wherein the second switch of the controller is in communication with at least the first EFD to restart the aeration cycle.

Example 14

The system of Example 11, wherein the controller includes a processor, wherein the processor is configured to coordinate operation of both the first EFD and the second EFD.

Example 15

The system of Example 14, wherein the processor is configured to alternatingly transition both the first EFD and the second EFD between the active state and the waiting state to provide an aeration cycle.

Example 16

The system of Example 15, wherein the processor is configured to alternatingly transition both of the first EFD and the second EFD between the active state and the waiting state to provide an aeration cycle.

Example 17

The system of Example 14, wherein the first EFD is configured to drive at least the marker material from the first portion to the second portion when the first EFD is in the active state, wherein the second EFD is configured to drive at least the marker material from the second portion to the first portion when the second EFD is in the active state.

Example 18

The system of Example 14, wherein the first EFD is configured to be in the active state when the second EFD is in the waiting state, wherein the second EFD is configured to be in the active state when the first EFD is in the waiting state.

Example 19

The system of any one or more of Examples 11 through 18, wherein the first portion or the second portion is configured to receive about 10 cc of the marker material.

Example 20

The system of any one or more of Examples 11 through 19, wherein the first portion or the second portion is configured to receive about 2 cc of air.

Example 21

A method of manufacturing a marker comprising: connecting to each other first and second containers associated with respective first and second electronic fluid dispensers (EFDs); initiating an aeration cycle with the first and second EFDs such that marker material is moved back and forth between the first and second containers to create an aerated marker material.

Example 22

The method of Example 21, prior to the step of connecting, further comprising: inserting gas in one container; inserting the marker material in the other container.

Example 23

The method of any one or more of Examples 21 through 22, wherein each container includes a male luer connector and wherein the step of connecting includes connecting the male luer connectors of the first and second containers to a female-female luer coupler.

Example 24

The method of any one or more of Examples 21 through 23, further comprising programming a dispense cycle of each EFD; and the step of initiating an aeration cycle includes feeding an output of one EFD indicating an end of a dispense cycle to an input of the other EFD indicating an initiation of a dispense cycle.

Example 25

The method of Example 24, wherein the step of programming the dispense cycle of each EFD includes programming each EFD with identical parameters.

Example 26

The method of Example 21, wherein after the step of initiating an aeration cycle, further comprising: transferring the aerated marker material to a plurality of smaller containers; inserting a marker element in each of the smaller containers; dehydrating the aerated marker material containing the marker element to create the marker.

Example 27

The method of Example 21, further comprising: monitoring the quality of aeration in the marker material; stopping the aeration cycle based on the monitored quality of aeration.

Example 28

The method of Example 21, wherein the marker material includes hydrogel, further comprising: inserting air in one container; inserting the hydrogel marker material in the other container in an amount which is at least two times the amount of the inserted air.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a marker comprising:
   connecting to each other first and second containers associated with respective first and second electronic fluid dispensers (EFDs);
   initiating an aeration cycle with the first and second EFDs such that marker material is moved back and forth between the first and second containers to create an aerated marker material.

2. The method of claim 1, prior to the step of connecting, further comprising:
   inserting gas in one container;
   inserting the marker material in the other container.

3. The method of claim 1, wherein each container includes a male luer connector and wherein the step of connecting includes connecting the male luer connectors of the first and second containers to a female-female luer coupler.

4. The method of claim 1, further comprising:
   programming a dispense cycle of each EFD; and the step of initiating an aeration cycle includes feeding an output of one EFD indicating an end of a dispense cycle to an input of the other EFD indicating an initiation of a dispense cycle.

5. The method of claim 4, wherein the step of programming the dispense cycle of each EFD includes programming each EFD with identical parameters.

6. The method of claim 1, wherein after the step of initiating an aeration cycle, further comprising:
transferring the aerated marker material to a plurality of smaller containers;
inserting a marker element in each of the smaller containers;
dehydrating the aerated marker material containing the marker element to create the marker.

7. The method of claim 1, further comprising:
monitoring the quality of aeration in the marker material;
stopping the aeration cycle based on the monitored quality of aeration.

8. The method of claim 1, wherein the marker material includes hydrogel, further comprising:
inserting air in one container;
inserting the hydro gel marker material in the other container in an amount which is at least two times the amount of the inserted air.

* * * * *